United States Patent [19]

Graupe

[11] Patent Number: 5,016,635
[45] Date of Patent: May 21, 1991

[54] CONTROL OF FNS VIA PATTERN VARIATIONS OF RESPONSE EMG

[75] Inventor: Daniel Graupe, Highland Park, Ill.

[73] Assignee: Sigmedics, Inc. of Delaware, Northfield, Ill.

[21] Appl. No.: 277,323

[22] Filed: Nov. 29, 1988

[51] Int. Cl.$^5$ .................................................. A61B 5/05
[52] U.S. Cl. ..................................... 128/421; 128/733
[58] Field of Search ................... 128/421, 422, 423 R, 128/423 W, 733, 741, 419 S

[56] References Cited

U.S. PATENT DOCUMENTS

| | | | |
|---|---|---|---|
| 4,213,467 | 7/1980 | Stulen et al. | 128/733 |
| 4,291,705 | 9/1981 | Severinghaus et al. | 128/733 |
| 4,622,973 | 11/1986 | Agarwala | 128/421 |
| 4,669,477 | 6/1987 | Ober | 128/421 |
| 4,750,499 | 6/1988 | Hoffer | 128/421 |
| 4,753,246 | 6/1988 | Freeman | 128/731 |
| 4,805,636 | 2/1989 | Barry et al. | 128/421 |

OTHER PUBLICATIONS

"Electromyographic Control of Functional Electrical Stimulation in Selected Patients" by D. Graupe et al., published in *Orthopedics*, vol. 7, No. 7, Jul. 1984, pp. 1134-1138.

"EMG Response to Electrical Stimulation of Quadriceps in Upper-Motor-Nemron Paraplegics and its Employment to Control Levels of Stimulation at Onset of Fatigue", Graupe et al., *The Journal of Orthopaedic Surgical Techniques*, vol. 2, No. 1, 1986, p. 67.

*Primary Examiner*—William E. Kamm
*Assistant Examiner*—Scott M. Getzow
*Attorney, Agent, or Firm*—Sitrick & Sitrick

[57] ABSTRACT

Paraplegic patients and cetain other paralyzed patients who suffer from an upper motor unit spinal cord injury and undergo FNS (Functional Neuromuscular Stimulation) experience muscle fatigue within a time span that is usually shorter than is normal, but have no sensation of this fatigue due to paralysis. When FNS is used functionally, as is its implied purpose, to stand and walk, the patients need the support of a walker or canes or elbow crutches, and are unable to manually adjust FNS levels or pulse widths to compensate for that fatigue, since the time for this adjustment is exactly when the patients cannot divert attention and hands to anything else. Under FNS, the stimulated muscles produce an EMG (electromyographic) signal at the stimulated site, in response to that stimulation. This response-EMG undergoes pattern changes with the progression of fatigue. The present invention employs pattern recognition of the response-EMG where pattern parameters are identified whose variation with time is a function of the progression of muscle fatigue. This time variation is employed to adjust FNS pulse width and/or pulse level to compensate for that fatigue in an automatic manner that does not require the patient's attention. The present invention also provides for diagnostic uses of this pattern recognition, and for muscle contractions other than for standing or walking.

16 Claims, 2 Drawing Sheets

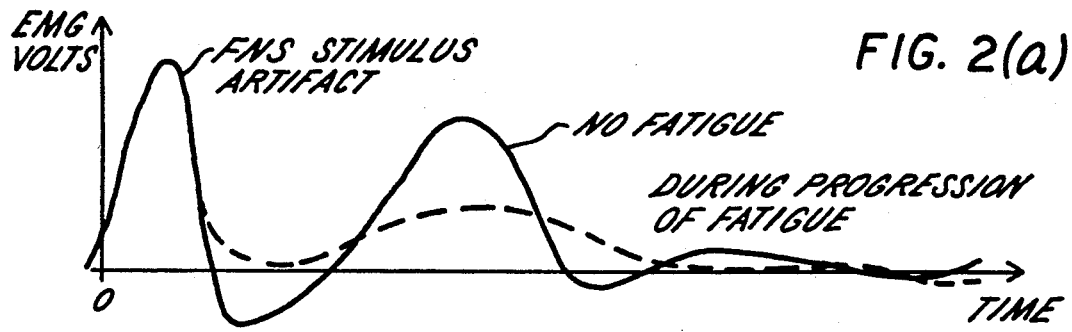
FIG. 2(a)
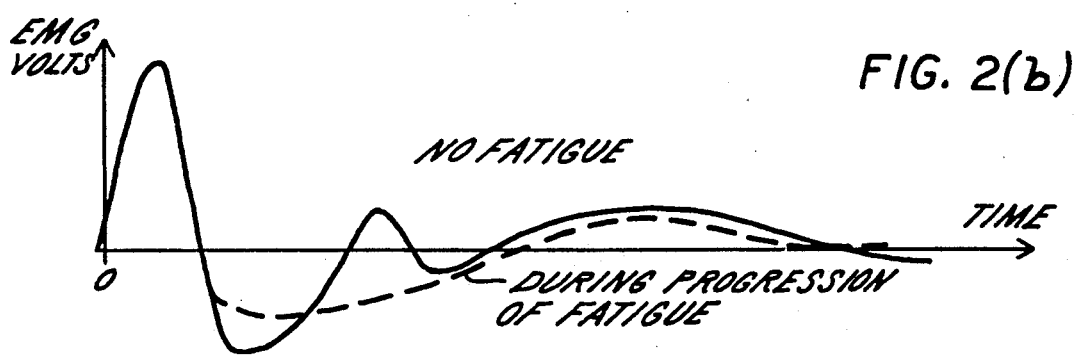
FIG. 2(b)
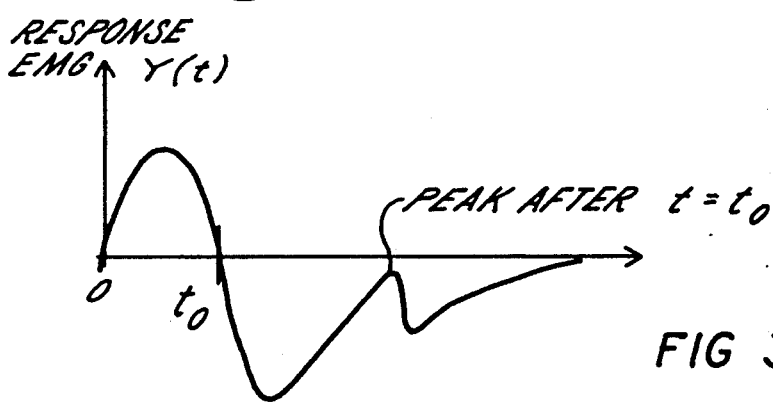
FIG 3(a) (BEFORE FATIGUE)
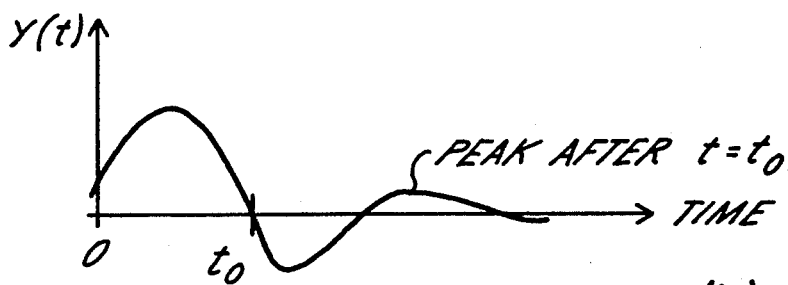
FIG. 3(b) (AFTER PROGRESSION OF FATIGUE)

CONTROL OF FNS VIA PATTERN VARIATIONS OF RESPONSE EMG

BACKGROUND OF THE INVENTION

This invention relates to functional neuromuscular stimulation (FNS) and more particularly to improved control of FNS.

Paraplegic patients and certain other paralyzed patients who suffered from an upper motor unit spinal cord injury and undergo FNS (Functional Neuromuscular Stimulation) experience muscle fatigue within a time span that is usually shorter than is normal, but they have no sensation of this fatigue due to their paralysis. Furthermore, when FNS is used functionally, as is its implied purpose, to stand and walk, the patients need the support of a walker or canes or elbow crutches, and are unable to manually adjust FNS levels or pulse widths to compensate for that fatigue, since the time when such adjustment is necessary is exactly when the patients cannot divert attention and hands to anything else. Work on electrical stimulation of paraplegics has been done by this inventor and by others.

References include:

[1.] Kralj, A., Electrical Stimulation of Lower Extremities in Spinal Cord Injury, *Proc. Nato Advance Studies Inst. On Spinal Cord Injuries*, Stoke Mandeville, England, 1981;

[2.] Kralj, A. et al. Electrical Stimulation Providing Functional Use of Paraplegic Patients' Muscles, *Med. Prog. Tech.*, Vol. 7, pp 3-9, 1980;

[3.] Liberson, W. T. et al, Functional Electrical Stimulation of the Peroneal Nerve Synchronized With the Swing Phase of the Gait of Hemiplegic Patients, *Arch. Phys. Med.*, Vol. 92, pp 101-105, 1961;

[4.] Graupe D. et al., Patient Controlled Electrical Stimulation Via EMG Signature Discrimination for Providing Certain Paraplegics with Primitive Walking Functions, *Journal Biomed. Eny.*, Vol., 5 pp 220-226, 1983;

[5.] Graupe, D. and Kohn, K. H. A Critical Review of EMG -Controlled Electrical Stimulation in Paraplegics CRC Crit. Rev. in Biomed. Eng., Vol. 15, pp 187-210, Mar. 1987; and,

[6.] Graupe, D. Identification of Systems, 2nd Edition, Krieges Publishing Co., Malabar, Fla., 1976.

Additionally, the present inventor has a pending U.S. patent application Ser. No. 014,389. In Reference [5], this inventor has shown that the surface (transcutaneous) response EMG as taken at the vicinity of the electrical stimulation sites in response to the stimuli applied at these sites, changes with the progression of the fatigue of the stimulated muscles during electrical stimulation.

Furthermore, it was explained in Reference [5] that the paraplegic patient has no sensation of his fatigue and of its progression, until his knee collapses from its extended (standing) position and bends, such that he falls down. When the patient's falling starts, the patient has no time nor has he the ability to use his hands nor his fingers to increase stimuli levels or sites of stimuli pulse width to overcome his fatigue. All he can do is at best to hold himself by his arms on the walker and thus achieve a somewhat controlled fall. The need for automatic monitoring of the muscle fatigue and of automatic (not manual) adjustment of stimulation to overcome this fatigue is therefore essential. A proposal for this adjustment is the subject matter of this inventor's U.S. patent application Ser. No. 014,389. In U.S. patent application Ser. No. 014,389 this adjustment is based on measuring and storing and comparing successive peaks in the response EMG and storing and comparing the time interval from the start of a given stimuli and the occurance of the peak in its corresponding response EMG signal. In many cases the peak may be higher after considerable muscle fatigue has set in, then immediately after stimulation level adjustment. In other cases no peak at all is formed prior to onset of fatigue. Hence this invention also covers situations when no peaks are considered or when the highest peak is not neccessarily occuring prior to onset of fatigue i.e., when lower peaks do not indicate progression of muscle fatigue.

BRIEF DESCRIPTION OF THE DRAWINGS

The present invention can be more clearly understood by reference to the detailed description in conjunction with the drawings, wherein:

FIGS. 2A and 2B illustrate two patterns of typical response-EMG signals at FNS-stimulated quadriceps muscles, and, FIGS. 3(a) and 3(b) illustrate Response-EMG waveforms before and after fatigue.

SUMMARY

Figure 1:
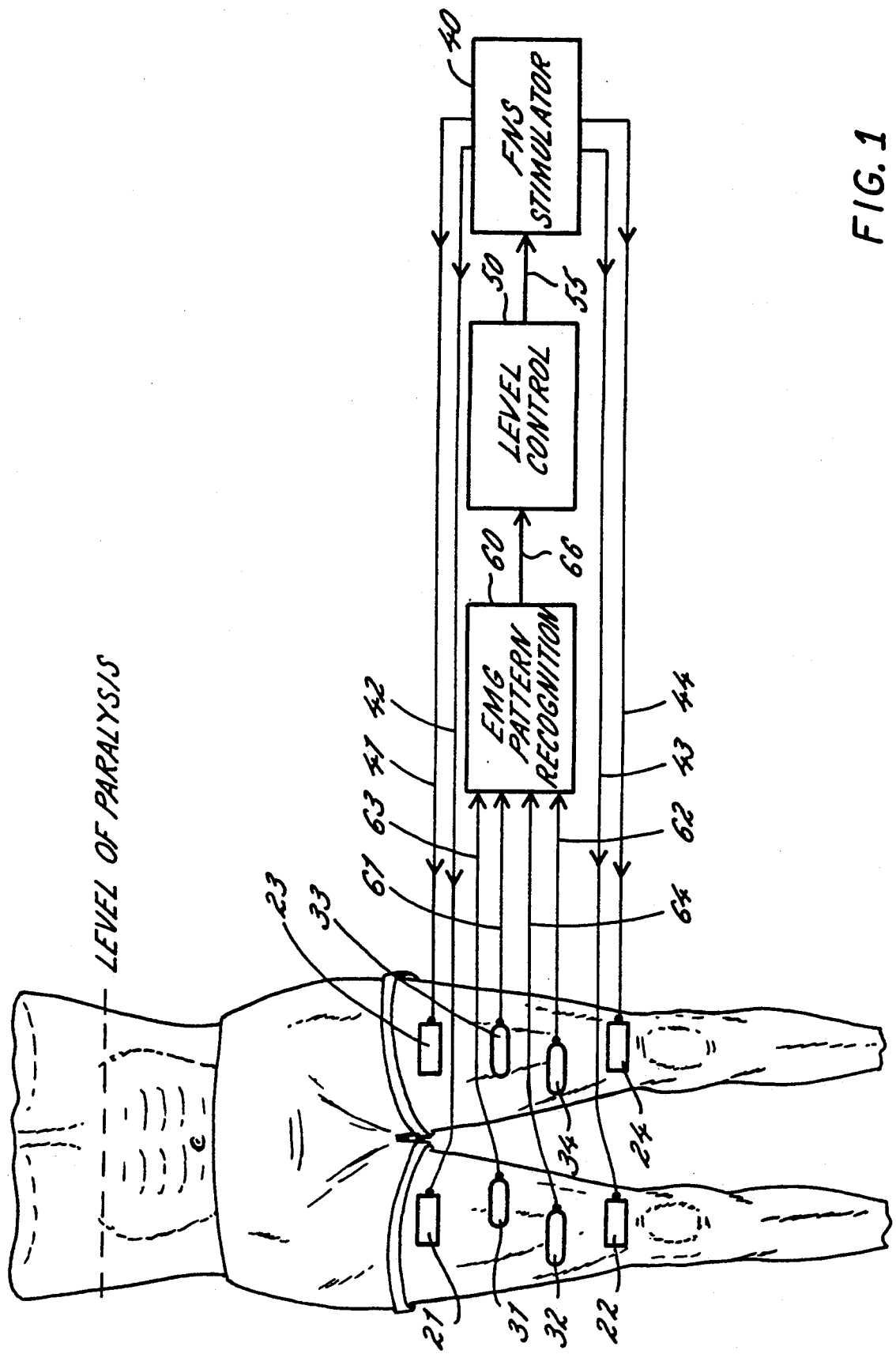
FIG. 1 illustrates a response EMG controlled FNS system coupled to a patient.

Under FNS, the stimulated muscles produce an EMG (electromyographic) signal at the stimulated site, in response to that stimulation, even in paralyzed parts of the body. This response-EMG undergoes pattern changes with the progression of muscle fatigue. The present invention employs pattern recognition of the response-EMG where pattern parameters are identified whose variation with time is a function of the progression of muscle fatigue. This time variation is employed to automatically adjust FNS pulse width and/or pulse level to compensate for that fatigue in an automatic manner that does not require the patient's attention. Additional embodiments of the present invention provide for diagnostic uses of this pattern recognition, and for muscle contractions other than for standing or walking.

The present invention is especially beneficial for upper motor neuron paraplegic patients, certain quadraplegics, stroke patients and cerbral palsy patients.

In accordance with the present invention, an improved system and method of automated control of Functional Neuromuscular Stimulation (FNS) is provided for responsive to pattern variations of the Response-EMG (electromyographic) signal produced by the muscle in response to the FNS.

DETAILED DESCRIPTION OF THE DRAWINGS

Referring to FIG. 1, a paraplegic patient 10 has electrodes 21, 22, 23 and 24 and sensors 31, 32, 33 and 34, attached to his (or her) legs 12, such as by an electrode gel. Electrodes 21, 22, 23 and 24 are coupled by electrical leads 41, 42, 43 and 44, respectively, to an FNS stimulator 40. Sensors, 31, 32, 33 and 34 are also attached to the patients leg 12, such as by an electrode gel, and are coupled via electrical leads 61, 62, 63 and 64 respectively, to an EMG Pattern Recognition Subsystem 60. The sensors 31 to 34 provide Response-EMG signals for coupling to the EMG Pattern Recognition Subsystem 60. The EMG Pattern Recognition Subsystem 60 analyzes the Response EMG signals, as discussed hereinafter, and outputs a first control signal, 66, coupled to a FNS Level/Pulse Width Controller 50, which responsive thereto outputs a second control signal, 55, coupled to the FNS Stimulator Subsystem 40. The FNS Stimulator 40 automatically adjusts the level and/or pulse width of the FNS signal outputs 41, 42, 43 and 44 responsive to the second control signal 55 as output from the FNS Controller 50.

Thus, FIG. 1 illustrates a functional neuromuscular stimulation system. The FNS electrodes 21–24 are coupled to the skin at the vicinity of a muscle to be stimulated. The FNS stimulation subsystem selectively outputs FNS stimulus signals 41 to 44 coupled via leads 41 to 44 to the FNS electrodes 21 to 24. The EMG electrodes 31 to 34 are coupled in the vicinity of the muscle to be stimulated, for sensing response-EMG signals responsive to the FNS stimulation subsystem. An EMG pattern recognition subsystem selectively analyzes multiple Response-EMG signals over time, and selectively provides FNS control signals 51 to 54 via electrical leads 51 to 54 responsive to recognized deviations beyond a predefined threshhold level of change in patterns of the response-EMG signals, where the changes of the pattern over time are changes relative to the EMG pattern within a specified small time interval after initial application of the FNS stimuli, and after each successive readjustment of FNS stimuli.

An FNS adjustment subsystem adjusts the FNS stimulus signals responsive to changes over time in the EMG pattern as recognized by said EMG pattern recognition means, so as to prevent fatigue. The FNS and EMG electrodes are preferably attached to the surface of the skin, such as by use of an electrode gel. However, the FNS and EMG electrodes can alternatively be implanted beneath the surface of the skin. Pattern recognition can be accomplished in terms of measuring the pointwise difference over a given fixed number of points in the response-EMG voltage vs. time signals as obtained at the response-EMG electrodes between their voltage values at discrete time points immediately after any adjustment of stimulus level vs. the corresponding value at any time later when fatigue may have started to take effect. The time scales are all with respect to the time instant of the initiation of each stimulus in a train of FNS stimuli, where each point considered in the two patterns that are compared is the same distance from the time instant of initiation point for each pattern. As one alternative to the above, the area differences rather than pointwise differences are considered as the selected parameter to be analyzed as between EMG patterns.

Numerous alternate systems can be constructed in accordance with the teachings of the present invention. The methodology is as follows.

FNS electrodes are attached to the patient's legs, and coupled to a FNS stimulator subsystem, which periodically outputs electrical stimuli. EMG electrodes are attached to the patient's legs, coupled to an EMG pattern recognition subsystem which analyzes the response-EMG signals and responsive thereto selectively outputs a FNS adapted control signal. The FNS stimulator subsystem outputs stimulus signals to the FNS electrodes which are modified responsive to the control signal, so as to prevent fatigue in the patient.

EMG signals are sensed from stimulated muscles as a response-EMG signal. The dynamic pattern of the response-EMG signals are repeatedly monitored over time and analyzed. A finite set of parameters associated with the pattern and capable of indicating a propensity of fatigue are analyzed. When at least one of said parameters has a significant change beyond a predetermined minimum value, indicative of fatigue, the control signal is provided to the FNS stimulator subsystem so as to modify the FNS stimuli coupled to the FNS electrodes so as to prevent fatigue. The finite set of parameters can be determined in accordance with a least squares polynomial fit to the response-EMG signal such as defined in Chapter 5 of Reference [6] set forth in the Background of the Invention herein. The finite set of parameters can be determined in terms of a transfer function fit to the response-EMG, where the response-EMG is considered as an impulse response, such that the transfer function becomes the inverse Laplace transform calculated for that impulse response which is the response-EMG pattern of EMG voltage vs. time, starting at the time instant at which the stimulus impulse is being applied by the stimulator.

Alternatively, the finite set of parameters can be determined by analysis of deviation of the response-EMG pattern from its mean over time. Alternatively, the finite set of parameters can be determined by means of analysis of said response-EMG signal by analysis of differences between successive extrema of said pattern over time.

In accordance with the present invention, an improved system and method auto overcomes loss of balance with the progress of muscle fatigue, by using response-EMG control of FNS in paraplegics who are standing or walking with cane or walker or elbow-crutch support. The importance of such control in paraplegics is obvious, since paraplegics have no sensation of muscle fatigue. When muscle fatigue has already caused loss of balance, in terms of knee bending, it is too late for the patient to adjust FNS levels or pulse width to strengthen stimulation. Furthermore, when balance is lost, the patient cannot take his hands off his walker or crutches to adjust the FNS level or pulse width, nor can he even afford to divert his attention to perform such an adjustment.

Use of EMG control of FNS has been proposed using EMG signals from the stimulated muscles (i.e., "response-EMG") where the first or second peak of the EMG signal is employed. However, such peaks are widely varying in value and the EMG's shape may differ from patient to patient. But, as taught by the present invention, in all situations, the dynamic pattern of the response-EMG does change. Hence, in accordance with the present invention, pattern identification of this EMG is performed in terms of a finite set of parameters, $p_1 \ldots p_n$, and progression of fatigue is determined by repeatedly monitoring these parameters over time, such that when at least one significant parameter changes beyond a predetermined minimal percentage value, fatigue is considered to exist to a degree that requires automatic increase in FNS level and/or pulse width.

For example, pattern recognition can be in terms of parameters of a least squares polynomial fit to the EMG pattern or in terms of a transfer function fit. Since recognition is of differences between patterns (i.e., between patterns before and during muscle fatigue), recognition of differences can be directly implemented by measuring the point-wise difference either between the before and during curves of the response-EMG as in either FIGS. 2A as obtained before and during muscle fatigue for successive points starting at the time of applying each stimulus to provide a time reference for comparison. In one embodiment, this can also be with respect to deviation of the pattern from its mean.

In the simplest case differences between areas under the patterns of the response-EMG before and during the progression of fatigue can be so considered.

In accordance with the present invention specific parameters of response EMG area are employed rather than peaks.

With the use of response EMG area, its integral over time clearly changes (its always decreases so the change is uni-directional) with the progression in all situations. These results have been empirically measured over several years, with examples as shown in FIG. 2.

Hence while there are many situations where peaks in the EMG signal will lead to a totally erroneous conclusion regarding fatigue, the area (integral over time) of the response-EMG always yields the correct conclusion.

Note that both the area and the peak of the response-EMG are measured from time $t_0$, not from time $t=0$, since between $t=0$ and $t=t_0$, we only have the artifact of the stimulus and not the response-EMG. Note that in FIG. 3 (a) the highest value of the response-EMG after $t=t_0$ is not a peak at all, whereas the local maximum (local peak) in FIG. 3(a) is below the peak of FIG. 3(b).

The present invention utilizes change in pattern recognition parameters, not maximal values or peaks. In the case of the present invention, changes in specified pattern recognition parameters or in area are the factor that determines fatigue. Neither area or pattern recognition parameters need peak (reach maximum) in the non-fatigued response EMG in the present invention. However, when area is considered they always happen (but need not) to be maximal at the non-fatigued situation. Other pattern recognition parameters are not always maximal in the non-fatigued situation, but can be utilized in accordance with the present invention.

In all cases the controller considers the pattern before fatigue to be that response-EMG pattern (solid line in FIGS. 2A-2B) obtained immediately following the first switching on of the stimulation or immediately following any increase in stimulations level whereas the EMG pattern (dashed lines in FIGS. 2A-B) during the progression of fatigue is considered to be any response-EMG pattern at the same electrode location at any time later. All patterns are compared as patterns of EMG voltage vs. time, where time is measured starting from the time $t_0$ at which any stimulation pulse is initiated or re-initiated by the stimulator, noting that these stimuli are applied and re-initiated at successive time intervals varying from between 20 and 50 milliseconds.

Referring to FIGS. 2A and 2B, two typical Response-EMG signal waveforms, as sensed by sensors 31-34, at FNS stimulated quadraceps muscles, are illustrated. Numerous other waveform patterns may also occur. The first peak in each waveform represents the FNS Stimulation Artifact. The solid line waveforms represent the response-EMG pattern under no fatigue conditions. The dashed line waveforms represent progression of muscle-fatigue conditions, measured at later times, which are sensed and utilized in accordance with the present invention, as described hereinabove.

While there have been described herein various embodiments and illustrations of the present invention, it will be understood by those skilled in the art that various other embodiments and adaptations are possible. Therefore, the scope of this invention is not limited to the disclosed embodiments, but is to be construed by the broadest reading of the appended claims.

What is claimed is:

1. A functional neuromuscular stimulation system comprising:
   FNS electrodes for coupling to the skin at the vicinity of a muscle to be stimulated;
   FNS stimulation means for selectively outputting FNS stimulus signals coupled to said FNS electrodes;
   Stimulus-Response-EMG electrodes for coupling in the vicinity of said muscle to be stimulated, for sensing Response-EMG signals responsive to said FNS stimulation means;
   EMG pattern recognition means for recognition of fatigue patterns for selectively analyzing multiple Response-EMG signals and for selectively providing FNS control signals responsive to recognized deviations beyond a predefined threshhold level of change in patterns of said Response-EMG signals wherein said changes of said pattern over time are changes relative to an EMG reference pattern which is the pattern of the response EMG within a specified small time interval after initial application of the FNS stimuli, and after each successive readjustment of FNS stimuli wherein pattern recognition is in terms of measuring the point wise difference over a given fixed number of points in the Response-EMG voltage vs. time signals as obtained at the Response-EMG electrodes between their voltage values at discrete time points immediately after any adjustment of stimulus level vs. the corresponding value at any time later when fatigue may have started to take an effect, wherein the time scales are all with respect to the time instant of the initiation of each stimulus in a train of FNS stimuli, and wherein each point considered in the two patterns that are compared is the same distance from the time instant of initiation point for each pattern; and,
   FNS adjustment means for automatically adjusting the FNS stimulus signals responsive to the pattern recognition means responsive to changes over time in the EMG pattern as recognized by said EMG pattern recognition means, so as to prevent fatigue.

2. The system as in claim 1 wherein said FNS electrodes are further characterized as being of the type for coupling to the surface of the skin.

3. The system as in claim 1 wherein said FNS and EMG electrodes are further characterized as being of the type for implantation beneath the surface of the skin.

4. The system as in claim 1 wherein said EMG electrodes are further characterized as being of the type for coupling to the surface of the skin.

5. The system as in claim 1 wherein said EMG electrodes are further characterized as being of the type for implantation beneath the surface of the skin.

6. The system as in claim 1 wherein said adjustment means provides for adjustment of FNS signals by adjusting FNS stimuli pulse width.

7. The system as in claim 1 wherein said adjustment means provides for adjustment of FNS signals by adjusting FNS stimuli amplitudes.

8. The system as in claim 1 wherein pattern recognition is in terms of measuring said point wide difference and where a function of the absolute value of said point wide difference is summed up to comprise a function of area differences over a given fixed number of points in the Response-EMG voltage vs. time signals as obtained at the Response-EMG electrodes between their voltage values at discrete time points immediately after any adjustment of stimulus level vs. the corresponding value at any time later when fatigue may have started to take an effect, wherein the time scales are all with respect to the time instant of the initiation of each stimulus in a train of FNS stimuli, and wherein each point considered in the two patterns that are compared is the same distance from the time instant of initiation point for each pattern.

9. A method of functional neuromuscular stimulation comprising the steps of:
   Electrically stimulating selected muscles;
   Sensing Response-EMG signals from said stimulated muscles;
   Repeatedly monitoring over time and analyzing the dynamic pattern of the Response-EMG signals;
   Identifying a finite set of parameters associated with said pattern, wherein said finite set of parameters is determined in terms of a transfer function fit to the Response-EMG, where the Response-EMG is considered as an impulse response, such that the transfer function becomes the inverse Laplace transform calculated for that impulse response which is the Response-EMG pattern of EMG voltage vs. time, starting at the time instant at which the stimulus impulse is being applied by the stimulator;
   Detecting when at least one of said parameters has a significant change beyond a predetermined minimum threshold value; and
   Adjusting said electrical stimulation responsive to said detecting.

10. The method as in claim 9 wherein said finite set of parameters is determined by analysis of deviation of the Response-EMG pattern from its mean over time.

11. A functional neuromuscular stimulation system comprising:
   means for selectively and adjustably electrically stimulating selected muscles;
   means for sensing Response-EMG signals from said stimulated muscles;
   means for repeatedly monitoring over time and analyzing the dynamic pattern of the Response-EMG signals;
   means for identifying a finite set of parameters associated with said pattern wherein said finite set of parameters is determined in terms of a transfer function fit to the Response-EMG, where the Response-EMG is considered as an impulse response, such that the transfer function becomes the inverse Laplace transform calculated for that impulse response which is the Response-EMG pattern of EMG voltage vs. time, starting at the time instant at which the stimulus impulse is being applied by the stimulator;
   means for detecting when at least one of said parameters has a significant change beyond a predetermined threshold minimum value; and;
   means for automatically modifying said electrical stimulation so as to prevent fatigue in said stimulated muscle, responsive to said means for detecting.

12. The system as in claim 11 wherein said electrical stimulation is comprised of a plurality of pulses having definable electrical characteristics of voltage level, duration and time spacing, wherein said means for modifying is further comprised of:
   means for varying at least one of said electrical characteristics responsive to said means for detecting.

13. The system as in claim 11 wherein said means for identifying is further comprised of:
   means for selecting a voltage versus time varying signal characteristic as a selected parameter of said Response-EMG signal, which characteristic changes in a detectable manner indicating the propensity for muscle fatigue conditions in said stimulated muscle, said system further characterized wherein said means for detecting is responsive to said selected parameter.

14. A diagnostic neuromuscular system for diagnosing rate and degree of muscle fatigue comprising:
   EMG electrodes for coupling in the vicinity of a muscle, for sensing Response-EMG signals from said muscle;
   EMG pattern recognition means including means for recognizing Response-EMG deviations for selectively analyzing multiple Response-EMG signals and for selectively providing output signals indicative of degree and rate of fatigue responsive to recognized deviations beyond a predefined threshold level of change in patterns of said Response-EMG signals wherein said changes of said pattern over time are changes relative to the Response-EMG pattern within a specified small time interval after an initial time.

15. The system as in claim 14 wherein pattern recognition is in terms of measuring the point wise difference over a given fixed number of points in the Response-EMG voltage vs. time signals as obtained at the Response-EMG electrodes between their voltage values at discrete time points immediately after any said initial time reference vs. the corresponding value at any time later when fatigue may have started to take an effect, wherein the time scales are all with respect to, said initial time reference and wherein each point considered in the two patterns that are compared is the same distance from the time instant of initiation point for each pattern.

16. The system as in claim 14 wherein pattern recognition is in terms of measuring the area difference over a given fixed number of points in the Response-EMG voltage vs. time signals as obtained at the Response-EMG electrodes between their voltage values at discrete time points immediately after any said initial time reference vs. the corresponding value at any time later when fatigue may have started to take an effect, wherein the time scales are all with respect to said initial time reference, and wherein each point considered in the two patterns that are compared is the same distance from the time instant of initiation point for each pattern.

* * * * *